United States Patent [19]

Seitz, Jr.

[11] Patent Number: 4,877,033

[45] Date of Patent: Oct. 31, 1989

[54] DISPOSABLE NEEDLE GUIDE AND EXAMINATION SHEATH FOR TRANSVAGINAL ULTRASOUND PROCEDURES

[76] Inventor: H. Michael Seitz, Jr., 214 Airdale Road, Rosemont, Pa. 19010

[21] Appl. No.: 190,059

[22] Filed: May 4, 1988

[51] Int. Cl.$^4$ .............................................. A61B 10/00
[52] U.S. Cl. .................................. 128/660.05; 128/4; 128/846; 604/171
[58] Field of Search ................ 128/3, 4, 6, 23, 303 R, 128/660.05, 660.06, 846; 604/22, 171, 96–99

[56] References Cited

U.S. PATENT DOCUMENTS

| | | | |
|---|---|---|---|
| 1,089,805 | 3/1914 | Wolf | 604/99 |
| 1,120,549 | 12/1914 | Schellberg | 604/171 |
| 3,794,042 | 2/1974 | DeKlotz et al. | 604/171 X |
| 3,809,072 | 5/1974 | Ersek et al. | 128/23 |
| 4,721,097 | 1/1988 | D'Amelio | 128/4 |
| 4,742,829 | 5/1988 | Law et al. | 128/660.06 |
| 4,779,611 | 10/1988 | Grooters et al. | 128/4 |

*Primary Examiner*—Dalton L. Truluck
*Attorney, Agent, or Firm*—Austin R. Miller

[57] ABSTRACT

A completely disposable apparatus of single unit construction designed for operative use in conjunction with a transvaginal ultrasound probe when performing transvaginal surgical procedures with ultrasonic guidance. This invention consists of a probe covering sheath containing a probe securing mechanism, an instrument or needle guide, and an ultrasound cable sleeve. When this unit is surgically sterilized and applied to the transvaginal ultrasound probe it provides an uninterrupted covering that permits the ultrasound probe and cable to be introduced into a sterile operative field while at the same time eliminating contamination of the ultrasound equipment with body fluids. Embodiments of the present invention provide a sterile plastic sheath to cover the transvaginal ultrasound probe during daily non-operative diagnostic examinations and a durable plastic sheath that when fitted over the transvaginal ultrsound probe protects it from accidental damage during storage.

17 Claims, 8 Drawing Sheets

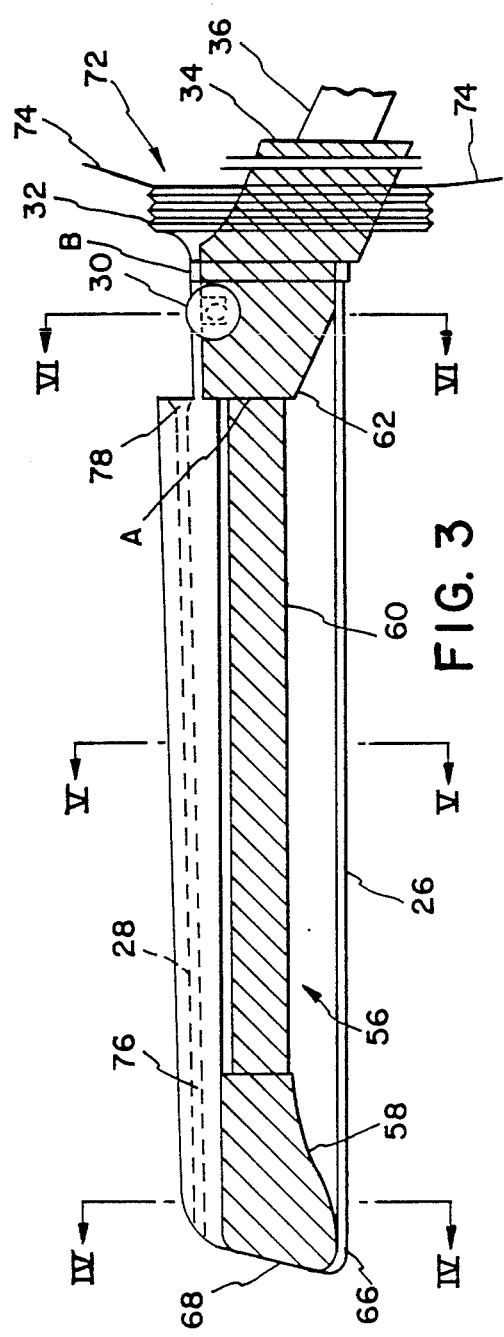

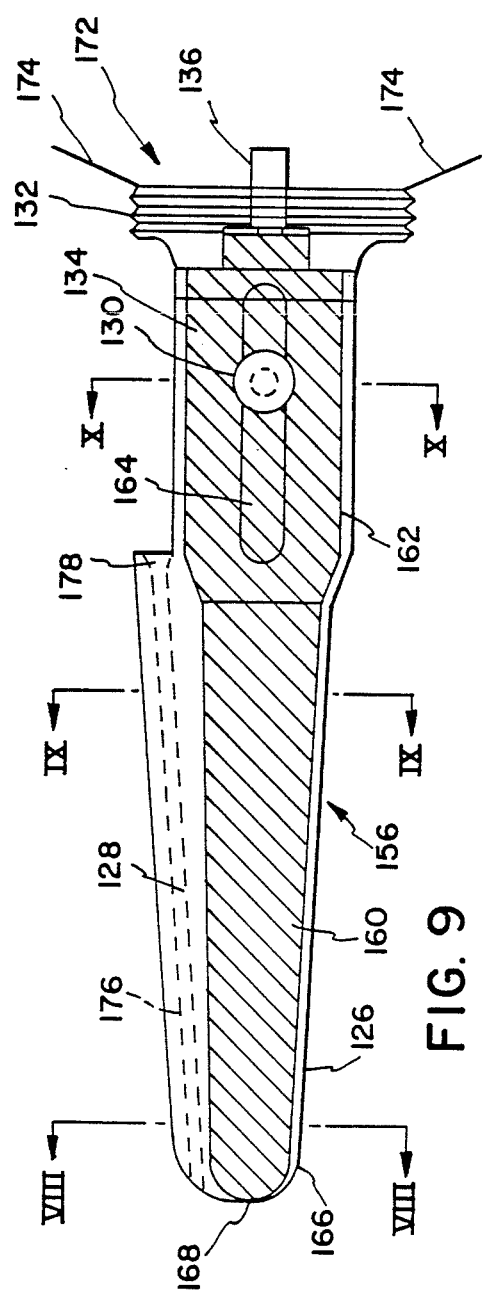
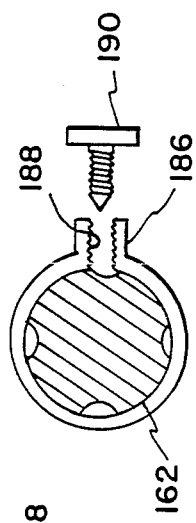
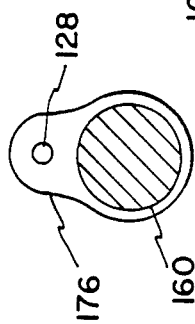
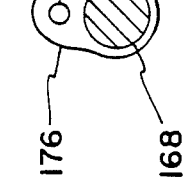
FIG. 9
FIG. 10
FIG. 9
FIG. 8

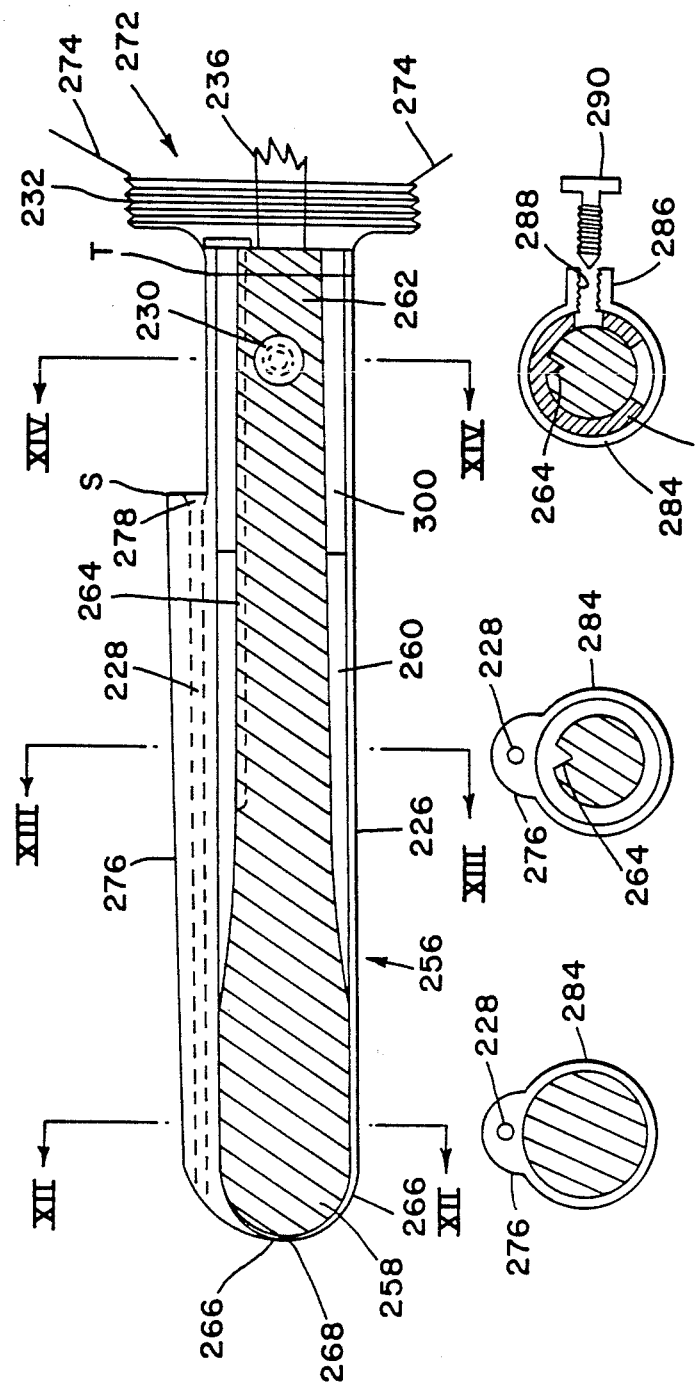

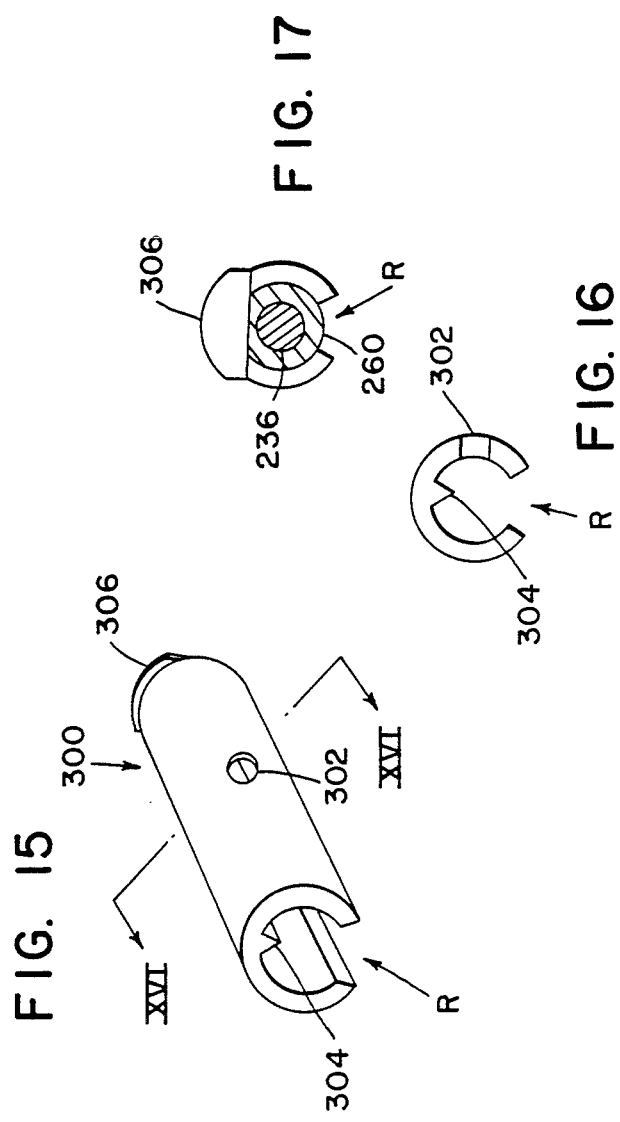

DISPOSABLE NEEDLE GUIDE AND EXAMINATION SHEATH FOR TRANSVAGINAL ULTRASOUND PROCEDURES

BACKGROUND OF THE INVENTION

1. Field of the Invention

The present invention relates in general to a disposable needle guide, ultrasound probe sheath and an ultrasound cable sleeve as a single unit designed for use in conjunction with a transvaginal ultrasound probe for a method of gynecologic surgery wherein fluid, tissue, and minute living organisms can be recovered from enclosed human body cavities without open surgery. Specifically, this invention is designed for use in an infertility procedure in which human eggs (ova) are retrieved transvaginally from the ovary for in vitro fertilization (IVF).

The introduction of ultrasonic equipment into the field of clinical medicine and surgery has contributed immeasurably to the physician's diagnostic and operative armamentarium. The recent addition of transvaginal ultrasound probes proved to be an invaluable aid in the performance of gynecologic procedures in general and, specifically, for in vitro fertilization (IVF) procedures. IVF involves removal of human eggs from the ovary at a precise time during the patient's menstrual cycle, transporting the eggs to a laboratory where they are artificially inseminated with the husband's spermatazoa. After 48 hours, those eggs that show definite evidence of normal fertilization (embryos) are placed into the uterine cavity of the patient through a small teflon catheter for possible implantation and pregnancy.

At the present time the most widely used method of recovering eggs from the human ovary utilized a transvaginal ultrasound probe. This procedure is considered to be an operative one because tissue is penetrated and a closed abdominal cavity is entered. Therefore, it must follow the usual guidelines of surgical sterility.

When performing transvaginal ovuum recovery procedures, the vaginal probe is fitted with a suitable sterile covering. Then, a sterile stainless steel needle guide is attached to the vaginal probe. The needle guide serves as a passageway for the introduction of an aspirating and flushing needle (or other suitable) instruments. The aspirating and flushing device disclosed in my copending application U.S. Ser. No. 135,701 filed Dec. 21, 1987, now U.S. Pat. No. 4,824,434 issued 4-25-89, and incorporated herein by reference, has been demonstrated to be ideally suited for this purpose. When the probe and guide are inserted deeply into the vaginal vault, the aspirating needle is introduced into the guide. Thereafter, when advanced, the needle need only penetrate the thin vaginal wall to gain access to the ovary located inside the abdominal cavity.

An ultrasound transducer located in the distal end of the vaginal probe makes possible the projection of a clear image of abdominal organs onto a nearby ultrasound screen. Direction and depth of the aspirating needle can be observed on the ultrasound screen and directed to the target ovarian follicle where vacuum aspiration of the egg-containing follicle is a relatively safe and simple manuver.

In experienced hands, the complication rate from this procedure is very low and, when complications are encountered, they are usually the result of either infection and/or internal bleeding induced by a misguided aspirating needle. Such complications, although relatively rare, may threaten the future reproductive capacity of the patient and prove to be quite costly in terms of patient welfare. An in-depth study of the transvaginal ultrasound equipment manufactured throughout the world, and the manner in which it is used, points out deficiencies in the prior are that favor the occurrences of the aforementioned complications that have not been fully rectified. Therefore, it is the purpose of the present invention and embodiments to effectively overcome the deficiencies existing in the prior art.

2. Description of the Prior Art

In the performance of transvaginal ultrasound probe procedures, whether diagnostic or operative, it appears that little attention is directed toward the avoidance of potential hazards of the transfer of sexually transmitted diseases (STD'S), some fatal, from one patient to another. The presence of human blood and vaginal secretion within the operative field provide a high risk environment for STD'S and requires that precautions be taken to insure that instruments that come into contact with these body fluids either be capable of adequate sterilization or discarded after each use for proper disposal. This becomes a problem when performing transvaginal operative procedures because the vaginal ultrasound probe and cable extending from it to the main ultrasound unit cannot be surgically sterilized.

As a result, many makeshift methods have evolved in an effort to provide a means whereby the transvaginal probe, needle guide and ultrasound cable can be covered with sterile material(s) enabling these items to be brought into a sterile operative area. Prior art designed for this purpose, employ a seperate covering sheath for the vaginal probe and a seperate sheath to envelope the ultrasound cable, as well as a seperate needle guide. These component parts are joined together with either sterile rubber bands or sterile adhesive tape. The sterile covering mechanism, if not of single unit construction, is a potential source for contamination of instruments, thereby creating the possibility of disease transmission.

Many clinics use a gas sterilized, commercially available condom to cover the vaginal probe in order to prevent probe contamination and provide a sterile probe surface. The practice of using a rubber condom is crude, offensive to many patients and frequently results in probe contamination due to breakage of the condom. When the probe becomes contaminated with blood and/or body fluids, cleansing is sometimes unreliable and time consuming. Some clinics use commercially available sandwich "baggies" to accomplish the same result. This too is subject to damage and contamination, as well as providing varying degrees of local discomfort to the patient.

Soaking the vaginal, probe in an, antiseptic solution prior to each use is frequently used, but is not totally effective in bringing about adequate sterilization and can prompt a local reaction or act as an irritant to delicate vaginal membranes of the patient. This practice is particularly undesirable when egg recovery procedures are performed, because of the possible toxic effect of the antiseptic solution on delicate human eggs. Moreover, prolonged soaking of the probe threatens the functional longevity of the ultrasound mechanism. In addition, soaking the probe before each use to achieve chemical sterilization requires the loss of valuable operating time.

Inasmuch as transvaginal operative procedures require maintenance of a sterile surgical area, it is necessary that the transvaginal probe handle and the ultrasound cable extending from it be covered by a sterile material. The prior art approaches this problem by providing a separate thin gauge plastic sleeve fitted over the cable and secured to the vaginal probe—again by tape or rubber bands.

Almost without exception, transvaginal ultrasound operative procedures are performed by using a reusable or permanent needle and/or instrument guide separate from the sheath covering the probe. A review of the world medical and surgical technology regarding transvaginal ultrasound probe units is presented in a special issue of CONTEMPORARY OBSTETRICS AND GYNECOLOGY, Vol. 30, Oct. 1987. Thirteen of the 14 manufacturers of ultrasonic equipment offer only the permanent or reusable guide. The reusable guide consists of a hollow stainless steel tubular design applied to the vaginal probe, either with the use of special clamps that can be secured to the probe or by fitting the guide into slots contained in the plastic probe housing.

Although the permanent needle guide can withstand surgical sterilization to permit it to be reused, there are several disadvantaged to this type of guide that far outweigh this advantage. The reusable or permanent needle guide is very costly, easily bent, and/or broken. Its practicality is severely restricted because it requires proper cleansing and sterilization after each use. When several operative procedures are scheduled in succession, either multiple needle guides are necessary or considerable valuable time is unnecessarily lost while awaiting sterilization between each procedure.

The potential for serious complications resulting from a misguided needle or instrument is great if the needle guide is not adequately secured to the vaginal probe. It is important that the needle guide, whether reusable or intended for one-time use only, be prevented from rotation or movement when positioned on the ultrasound probe. It is the needle guide that directs the position of the operative needle. If the guide becomes dislodged from the probe, needle or instrument control is lost.

I know of only one company to offer a disposal needle guide for use with their transvaginal ultrasound probe. Although the needle or instrument guide itself is disposable, the manner in which it is used in preparation of the vaginal probe for transvaginal ultrasound operative procedures is essentially the same as other prior art. It continues to use a modified sterile condom or sheath to cover the probe. A separate sterile plastic sleeve is supplied to cover the ultrasound cable.

This "snap-on" disposable needle guide is attached to the vaginal probe over the rubber probe sheath and relies only on the guide fitting into a slot provided in the vaginal probe housing. Several deficiencies are readily apparent. The cylindrical ultrasound probe shaft provides potential for lateral rotation of the "snap-on" cylindrical needle guide. Stability of the securing mechanism of the guide is open to serious question inasmuch as the rubber sheath covering the probe shaft is interposed between the needle guide and the shaft, thereby making adequate fixation difficult.

In addition, the exist portal of the needle guide is located far behind the leading surface of the transvaginal probe head. This results in an undesirably large segment of the operating needle remaining unsplinted by the guide, thereby favoring the possibility of needle breakage or bending. This often results in misdirection of the advancing needle during operative procedures. The unsplinted needle portion should be minimal in order to protect the needle and maintain a straight and predictable operative path of the needle if complications are to be avoided. Another deficiency in this art is the use of a modified condom sheath to cover the probe head and shaft. Although an improvement over the commercially available condom, it is still subject to breakage with resultant contamination.

Still another deficiency is the fact that the ultrasound cable sleeve is a separate part of the device. When preparing the transvaginal ultrasound probe for operative use, application of each separate component part requires extra time and care in order to avoid contamination of either the surgeon or the probe covering. The present invention corrects these deficiencies found in the prior art.

When the transvaginal ultrasound probe is used only for daily diagnostic examinations wherein penetration of tissue is not required, it is not essential that an elaborate sterile operative field be maintained. Nor is it essential that the ultrasound cable be shielded with a sterile cover. A needle or instrument guide is not required. The prior art continues to employ a sterile rubber condom or sterile plastic "baggie" for this purpose. Ideally, the operative sheath should be surgically sterile, easy to apply and remove, constructed of a material that eliminates breakage and contamination and designed for one-time use only. An extension of the present invention satisfies these criteria and thereby overcomes the stated deficiencies in the prior art.

To date, there are no known references in the prior art regarding a protective device to guard against accidental damage to the transvaginal probe when not in use. The transvaginal probe being constructed of plastic is subject to breakage, thereby rendering the instrument inoperable. An extension of the present invention is provided to guard against probe damage, thereby eliminating costly repairs and the loss of substantial operative use of equipment.

OBJECTS OF THE INVENTION

It is a primary object of the present invention to provide a disposable, operative sheath of single unit construction that contains a needle and/or instrument guide and a sleeve for covering the ultrasound cable for use in procedures employing the transvaginal ultrasound probe.

It is another object of the present invention, when attached to the ultrasound probe, to permit introduction of an aspirating and flushing needle used in IVF procedures, as well as other surgical instruments for general operative use.

It is still another object of the present invention, when surgically sterilized, to provide an effective sterile covering for the transvaginal probe and ultrasound cable when used within a sterile operative field, as well as preventing the contamination of these items.

It is another object of the present invention to provide a needle and instrument guide wherein a minimal portion of the needle or instrument exiting from the needle guide is unshielded by the needle guide housing before it is advanced into the operative area.

It is a further object of the present invention to have the needle exit from the needle guide as close to the leading surface of the probe head as possible to avoid misdirection and/or damage to the needle or instruments being advanced.

It is still a further object of the present invention to provide a needle guide that, when applied to the transvaginal ultrasound probe, can be securely fixed to the probe so that no rotation of the needle guide is possible.

It is yet another object of the present invention to provide a locking mechanism to prevent forward and backward motion of the operative sheath when in position on the probe.

Another object of the present invention is to provide a needle guide sheath and unit which can be easily applied to and removed from the transvaginal ultrasound probe and discarded after one time use.

It is an object of another aspect of the present invention to provide a disposable non-operative examination sheath for use in diagnostic transvaginal ultrasound probe procedures that can quickly be applied to and removed from the transvaginal probe and prevents probe contamination as well as eliminates the transmission of disease.

It is still another object of an extension of the present invention to provide a durable storage sheath that when placed over the transvaginal ultrasound probe serves as a protective mechanism against accidental damage to the probe when not in use.

SUMMARY OF THE INVENTION

The present invention is a disposable plastic sheath of single unit construction which covers the vaginal probe and incorporates a needle guide and ultrasound cable sleeve designed for operative use with a transvaginal ultrasound probe. The main body of the invention consists of a rigid, break-resistant, plastic sheath of comfortable anatomic design that can be "glove-fitted" over the ultrasound probe.

The internal design of the plastic sheath is molded to conform to the configuration of the probe head, thereby preventing lateral rotation of the plastic sheath when in position over the probe. A lock mechanism located on the proximal end of the plastic sheath prevents forward and backward motion of the operative sheath when the lock is engaged into a slot contained in the probe housing. The plastic wall at the terminal end of the plastic sheath is closed and is of appropriate thickness so not to impede flow of ultrasonic sound waves therethrough. This enables projection of a clear image of intra-abdominal organs onto an ultrasound screen.

A small, hollow passageway located at the top of the cylindrical plastic sheath (12 o'clock) traverses substantially the entire length of the sheath and provides a means for introducing an aspirating and flushing needle, as well as other surgical instruments. The extreme proximal end of the plastic sheath is contiguous with a folded thin gauge plastic sleeve that, when opened, surrounds a large portion of the ultrasound cable. This plastic sleeve is sealed onto the plastic sheath, making the entire unit a single airtight system.

Another aspect of the present invention provides an effective means for prevention of transvaginal ultrasound probe contamination during routine non-operative transvaginal examination. The construction of the examining sheath is substantially the same as that of the needle guide unit, without the plastic sleeve and needle guide. When large numbers of diagnostic ultrasound probe examinations are performed in succession, it is desirable to minimize the time lost between each examination while guarding against contamination of either patient or transvaginal probe. Application of this device onto the transvaginal ultrasound probe is quick and simple and is to be discarded after each use.

A further aspect of the present invention is of similar construction to the diagnostic examination sheath, but is constructed of thicker and more durable walls and serves as a means of protecting the transvaginal ultrasound probe when not in use. The transvaginal ultrasound probe, being constructed of rigid plastic, is subject to physical damage. Such damage renders the probe inoperable. This incurs a valuable loss of operational time and patient inconvenience while awaiting costly repairs or replacement.

The operative sheath, including the needle guide and plastic sleeve, can be packaged and pre-sterilized with either gamma radiation or ethylene oxide gas for immediate use in the operating room. The quick and convenient method of application and removal of this unit, along with other time saving features, makes it not only a safe and efficacious device, but cost effective as well.

Prevention of the transmission of serious, and sometimes fatal, reproductive tract diseases from contaminated instruments incurred during the performance of operative and/or diagnostic transvaginal ultrasound procedures is of paramount importance and serves as a basis for the present invention and its embodiments.

BRIEF DESCRIPTION OF THE DRAWINGS

FIG. 3 is a schematic side view of a transvaginal ultrasound probe as shown in FIG. 2 and apparatus in accordance with the invention.

FIG. 4 is a cross sectional view of a transvaginal ultrasound probe and apparatus of the invention taken along the lines and arrows IV—IV in FIG. 3.

FIG. 5 is a cross sectional view of a transvaginal ultrasound probe and apparatus of the invention taken along the lines and arrows V—V in FIG. 3

FIG. 6 is a cross sectional view of a transvaginal ultrasound probe and apparatus of the invention taken along the lines and arrows VI—VI in FIG. 3.

FIG. 7 is a schematic side view of another embodiment of apparatus of the invention mounted over another transvaginal ultrasound probe as presently available.

FIG. 8 is a cross sectional view of a transvaginal ultrasound probe and apparatus of the invention taken along the lines and arrows VIII—VIII in FIG. 7.

FIG. 9 is a cross sectional view of a transvaginal ultrasound probe and apparatus of the invention taken along the lines and arrows IX—IX in FIG. 7.

FIG. 10 is a cross sectional view of a transvaginal ultrasound probe and apparatus of the invention taken along the lines and arrows X—X in FIG. 7.

FIG. 11 is a schematic side view of another embodiment of apparatus of the invention mounted over another transvaginal ultrasound probe as presently available.

FIG. 12 is a cross sectional view of a transvaginal ultrasound probe and apparatus of the invention taken along the lines and arrows XII—XII in FIG. 11.

FIG. 13 is a cross sectional view of a transvaginal ultrasound probe and apparatus of the invention taken along the lines and arrows XIII—XIII in FIG. 11.

FIG. 14 is a cross sectional view of a transvaginal ultrasound probe and apparatus of the invention taken along the lines and arrows XIV—XIV in FIG. 11.

FIG. 15 is a perspective view of an adaptor designed to fit over the transvaginal ultrasound probe shown in FIG. 11.

FIG. 16 is a cross sectional view of the adapter shown in FIG. 15 as taken along the lines and arrows XVI—XVI.

FIG. 17 is an end view of the adapter as shown in FIG. 15 fitted over the transvaginal ultrasound probe, taken in section, of FIG. 11.

DETAILED DESCRIPTION OF THE DRAWINGS

Figure 1:
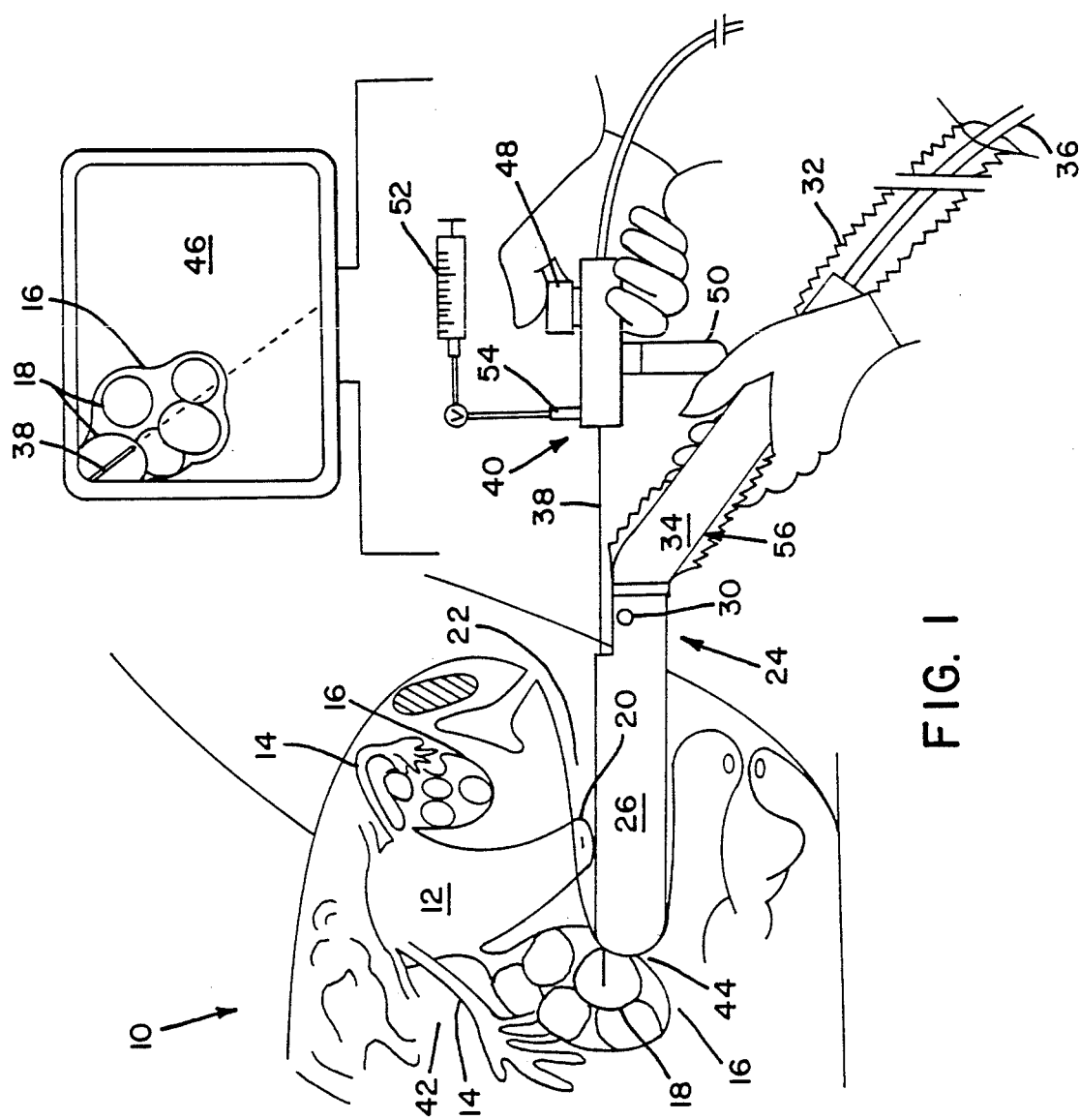
FIG. 1 is a schematic view of a transvaginal ultrasound ovum procedure utilizing apparatus in accordance of the invention.

Although a particular form of apparatus has been selected for illustration in the drawings, and although specific terms will be used in the specification, for the sake of clarity in describing the apparatus shown, the scope of this invention is defined in the appended claims and is not intended to be limited either by the drawings or the terms used in the specification or abstract.

FIG. 1 is a diagramatic representation of an IVF transvaginal ultrasound ovum retrieval procedure provided to assist the reader in developing a more in depth understanding of the nature and objectives of the present invention and their relationship to current transvaginal ultrasound procedures, both operative and nonoperative.

A lower portion of a human torso is generally designated by the number 10. A cross-sectional view of the human lower reproductive organs is shown. The organs consist of uterus 12, fallopian tubes 14, ovaries 16, ovarian follicles 18, cervix 20, and vagina 22. An ultrasound probe utilizing apparatus 24 of the present invention is shown inserted deeply into vagina 22 and is illustrated in the operative position. Although the transvaginal probe used in this particular illustration is one presently available for use with the supplier's own ultrasound unit, the substance of this invention and its embodiments is applicable for use with all models of transvaginal probes currently in use.

The present invention, designated as sheath 24, which is highlighted in the diagram, is shown covering ultrasound vaginal probe 56 (see also FIG. 2) and ultrasound cable 36. Main body 26 of the present invention envelops ultrasound probe 56 and consists of housing 76 having a hollow passageway 28 (see FIG. 3) which serves as a needle or instrument guide. In addition, main body 26 consists of sheath securing mechanism 30 and cable sleeve 32 and are contiguous therewith and are shown covering probe handle 34 and ultrasound cable 36. Presterilization of the present invention prior to its placement onto ultrasound probe 56 and cable 36 permits these items to be used in a sterile operating field and eliminates probe and cable contamination as well.

Needle 38 of an aspirating and flushing device 40, such as the device disclosed in my copending application Ser. No. 135,701, is shown extending through needle guide 28 and entering a fluid filled, egg containing, follicle 18 located on target ovary 16. Access to ovary 16 within abdominal cavity 42 is accomplished by simple needle penetration of thin vaginal wall 44. The position of needle 38 is monitored on ultrasound screen 46 which clearly outlines ovary 16 and follicle 18.

In the diagram of FIG. 1, needle 38 is shown inside ovarian follicle 16 on the screen. Aspirating and flushing device 40 is a closed tubular system which is attached to a continuous suction source not shown (120 mm. mercury). When suction "on-off" valve 48 is depressed simultaneous to the penetration of ovarian follicle 18 by needle 38, suction is actuated and the contents of follicle 18, including the human egg, are drawn into collecting vessel 50 of aspirating and flushing device 40. If the egg is not recovered in the initial aspirate, a flushing solution can be introduced to redistend follicle 18 by injecting fluid from syringe 52 into needle 38 by way of a side portal 54 on device 40. Following this, reaspiration can be performed as required.

Figure 2:
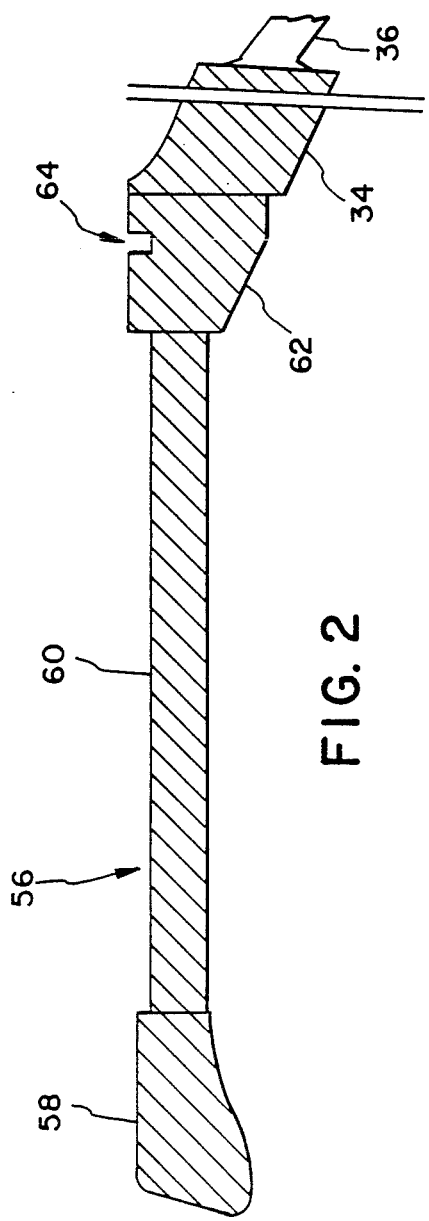
FIG. 2 is a schematic side view of a transvaginal ultrasound probe, as manufactured by one Company.

FIG. 2 is a schematic side view of transvaginal probe 56. In this illustration the probe serving as a model is provided for use with the supplirt's own ultrasound unit. Probe 56 consists of the probe head 58, shaft 60, base 62, base notch 64, handle 34 and ultrasound cable 36.

FIG. 3 is a schematic view of an embodiment of the present invention which is shown applied over transvaginal ultrasound probe 56 in position for operative use. Probe 56 is distinctively shaded in order to detail the relationship between the probe and the present invention. Main body 26 of the present invention is a thin walled, break resistant, cylindrical shaped rigid plastic sheath constructed to fit snugly over transvaginal probe head 58 and base 62. Main body 26 extends from the junction of probe base 62 and probe shaft 60 at point A to the terminal end of the probe.

The distal or terminal end 66 of main body 26 is a closed end which is contoured and slants preferably about 45° downward to provide a comfortable anatomic design. Although contiguous with the plastic wall of main body 26, the wall thickness in this area is reduced to an optimum gauge to create window 68 to permit free passage of ultrasound waves to and from the ultrasound transducer (not shown) located in probe head 58. The proximal end of main body 26 is open and contains sheath locking mechanism 30 and ultrasound cable sleeve 32.

Cable sleeve 32, shown in a folded position, is a thin gauge plastic tubular structure preferably cemented onto main body 26 at point B. The open or most proximal end 72 of sleeve 32 contains two plastic tabs 74 that extends from open end 72 of sleeve 32 that are provided to enable the surgeon or assistant to pull sleeve 32 over probe handle 34 and ultrasound cable 36 without contaminating him or herself when preparing probe 56 for operative use. When sleeve 32 is opened it preferably provides an elongated sterile cover that includes probe handle 34 and ultrasound cable 36 as shown in FIG. 1.

The plastic wall of main body 26 extends upwardly (12 o'clock) to form housing 76 through which hollow passageway 28 is constructed. Passageway 28 serves as a guide for operative needles and/or instruments. Proximal end 78 of passageway 28 is flared to facilitate the introduction of such instruments. The needle or instrument guide 28, extends from the distal end of base 62 of probe 56 to the terminal end of probe head 58.

The apparatus shown in FIG. 3 is broken into three cross sectional views, FIGS. 4, 5 and 6, for the purpose of illustrating the safe and efficient means for securing the present invention to transvaginal ultrasound probe 56 when in operative use. The interior design of main body 26 is molded to fit the exterior configuration of the probe head 56 as shown in FIG. 4. Probe head 58, has a semi-rectangular top surface 80 and a substantially round underside 82, which prevents lateral rotation of main body 26 when in position on probe 56. This is an important feature in preventing the undersirable movement of instrument guide 28. Housing 76 surrounding instrument guide 28 is of sufficient wall thickness to prevent the bending or breakage of instruments within guide channel 28.

FIG. 5 shows the relationship of main body 26 to probe shaft 60 when main body 26 is positioned on probe 56. Wall thickness of main body 26 in this area is such that walls 84 of main body 26 are supported to the extent that bending of main body 26 does not occur during operative use. The interior of walls 84 is shown substantially similar to that of FIG. 4 in order to permit probe head 58 to slide past walls 84.

Backward and forward movement of main body 26, when positioned on the vaginal probe 56, is prevented through securing mechanism 30, illustrated in FIG. 6. Securing mechanism 30 is located near the proximal open end of main body 26 and consists of a unilateral plastic housing arm 86, which is a molded extension of plastic wall 84 of main body 26. A through-and-through threaded channel 83 traverses housing arm 86 and permits introduction of set screw 90. Set screw 90 is preferably made of a plastic type or light metallic material. The General Electric transvaginal probe housing base 62 contains notched channel 64 on the upper most top portion of probe housing base 62 that extends across the entire width of probe base 62, as shown in FIG. 6. When set screw 90 is fully secured into threaded channel 88 it engages into base channel 64, thereby eliminating any undesirable to and fro movements of main body 26 when on transvaginal ultrasound probe 56.

FIG. 7 is a schematic side view of the present invention which is shown applied over transvaginal ultrasound probe 156 in position for operative use. In this illustration the probe serving as a model is manufactured by a different supplier. The probe is distinctively shaded in order to detail the relationship between the probe and the present invention. Probe 156 consists of combination probe head shaft 160, base 162, base notch 164, handle 134 and ultrasound cable 136.

Main body 126 of the shown embodiment of the present invention is a thin walled, break resistant, conically shaped rigid plastic sheath constructed to fit snugly over the transvaginal combination probe head shaft 160 and base 162. Main body 126 extends from the junction of probe base 162 and probe handle 134 at point x to the terminal end of the probe.

The distal or terminal end 166 of main body 126 is a closed end which is substantially roundly contoured to provide a comfortable anatomic design, and although contiguous with the plastic wall of main body 126, the wall thickness in this area is reduced to an optimum gauge to create window 168 designed to permit free passage of ultrasound waves to and from the ultrasound transducer (not shown) located in the combination probe head and shaft 160. The proximal end of main body 126 is open and contains sheath locking mechanism 130 and ultrasound cable sleeve 132.

Cable sleeve 132, shown in a folded position, is a thin gauge plastic tubular structure cemented onto main body 126 at point x. The open or most proximal end 172 of sleeve 132 contains two plastic tabs 164 that extend from proximal end 172 of sleeve 132 that are provided to enable the surgeon or assistant to pull sleeve 132 over ultrasound cable 136 without contaminating him or herself when preparing probe 156 for operative use. When sleeve 132 is opened it preferably provides an elongated sterile cover for ultrasound cable 136 as shown in FIG. 1.

The plastic wall of main body 126 extends upwardly (12 o'clock) to form housing 176 through which hollow passageway 128 is constructed. Passageway 128 serves as a guide for operative needles and/or instruments. Proximal end 178 of passageway 128 is flared to facilitate introduction of such instruments. Needle or instrument guide 128, extends from the distal end of base 162 of probe 156 to the terminal end of the combination probe head and shaft 160.

FIGS. 8, 9 and 10 are included for the purpose of illustrating the safe and efficient means for securing the present invention to transvaginal ultrasound probe 156 when in operative use. The interior design of main body 126 is molded to fit the exterior congiguration of the combination probe head and shaft 160 as shown in FIG. 8. Combination probe head and shaft 160 is substantially conically shaped. Housing 176 surrounding instrument guide 128 is of sufficient wall thickness to prevent bending or breakage of instruments within instrument guide 128.

FIG. 9 shows the relationship of main body 126 to the combination probe head and shaft 160 when main body 126 is positioned on probe 156. Wall thickness of main body 126 in this area is such that the walls of main body 126 are supported to the extent that bending of main body 126 does not occur during operative use.

Backward and forward movement of main body 126, when positioned on vaginal probe 156, is prevented through securing mechanism 130, illustrated in FIG. 10. Securing mechanism 130 is located near the proximal open end of main body 126 and consists of unilateral plastic housing arm 186, which is a molded extension of the plastic wall of main body 126. A through-and-through threaded channel 188 traverses housing arm 186 and permits the introduction of set screw 190. Set screw 190 is preferably made of a plastic type of light metallic material. The transvaginal probe housing base 162 contains notched channels 164, extending along probe housing base 162 as shown in FIG. 10. When set screw 190 is fully secured into threaded channel 188 it engages into notched channel 164, thereby eliminating any undesirable to and fro movements of main body 126 when on transvaginal ultrasound probe 156, as well as lateral rotation thereof.

FIG. 11 is a schematic side view of the present invention which is shown applied over transvaginal ultrasound probe 256 in position for operative use. In this illustration the probe serving as a model is manufactured by yet another supplier. The probe is distinctively shaded in order to detail the relationship between the probe and the present invention. Probe 256 consists of probe head 258, shaft 260, base 262 and ultrasound cable 236.

Main body 226 of the present invention is a thin walled, break resistant, cylindrically shaped rigid plastic sheath constructed to fit snugly over transvaginal probe head 258. Main body 226 extends from point P to the terminal end of the probe.

The distal or terminal end 266 of main body 226 is a closed end which is substantially round to provide a comfortable anatomic design. Although contiguous with the plastic wall of main body 226, the wall thickness in this area is reduced to an optimum gauge to create a window 268 designed to permit free passage of ultrasound waves to and from the ultrasound transducer (not shown) located in probe head 258. The proximal end of main body 226 is open and contains sheath locking mechanism 230 and ultrasound cable sleeve 232.

Cable sleeve 232, shown in a folded position, is a thin gauge plastic tubular structure cemented onto main body 226 at point T. The open or most proximal end 272 of sleeve 232 contains two plastic tabs 274 that extend from open end 272 of sleeve 232 that are provided to enable the surgeon or assistant to pull sleeve 232 over ultrasound cable 236 without contaminating him or herself when preparing probe 256 for operative use. When sleeve 232 is opened it preferably provides an elongated sterile cover that includes ultrasound cable 236 as shown in FIG. 1.

The plastic wall of main body 226 extends upwardly (12 o'clock) to form housing 276 through which hollow passageway 228 is constructed. Passageway 228 serves as a guide for operative needles and/or instruments. Proximal end 278 of passageway 228 is flared to facilitate introduction of such instruments. Needle or instrument guide 228 extends from point S to the terminal end of probe head 258.

FIG. 12, 13 and 14 are included for the purpose of illustrating the safe and efficient means for securing the present invention to transvaginal ultrasound probe 256 when in operative use. The interior design of main body 226 is molded to fit the exterior configuration of the probe head 258 as shown in FIG. 12. Housing 276 surrounding instrument guide 228 is of sufficient wall thickness to prevent bending or breakage of instruments within guide channel 228.

FIG. 13 shows the relationship of main body 226 to probe shaft 260 when main body 226 is positioned on probe 256. Wall thickness of main body 226 in this area is such that walls 284 of main body 26 are supported to the extent that bending of main body 26 does not occur during operative use. The interior of walls 284 is shown substantially similar to that of FIG. 12 in order to permit probe head 258 to slide past the walls.

Backward and forward movement of main body 226, when positioned on vaginal probe 256, is prevented by securing mechanism 230, illustrated in FIG. 14. Securing mechanism 230 is located near the proximal open end of main body 226 and consists preferably of an unilateral plastic housing arm 286, which is a molded extension of plastic wall 284 of main body 226. A through-and-through threaded channel 288 traverses housing arm 286 and permits introduction of set screw 290. Set screw 290 is preferably made of a plastic type or metallic material. The transvaginal probe housing base 262 and a portion of shaft 260 contain notched v-shaped channel 264 on the uppermost top portion that extends along the entire length of probe base 262, and partially along shaft 260 as shown in FIGS. 11 through 14. When set screw 290 is fully secured into threaded channel 288 it contacts base 262, thereby eliminating any undesirable to and fro movements of main body 226 when on transvaginal ultrasound probe 256.

Referring now to probe head 258 as shown in FIG. 12 and probe base 262 as shown in FIG. 14, the enlarged diameter of probe head 258 requires that the inner diameter of the entire length of main body 226 have a diameter sufficient to permit the introduction of probe head 258. This creates an undesirable space between main body 226 and base 262. Such a space reduces probe/sheath stability. This instability is eliminated by use of adaptor 300, which is shown in detail in FIG. 15 and described below.

Adaptor 300, shown in FIGS. 11 and 15, slides tightly over probe base 262. The inner diameter of adaptor 300 is molded to fit the external configuration of probe head 262. The lateral wall of adaptor 300, as shown in FIG. 15 contains hole 302 provided to receive set screw 290 contained in locking mechanism 230 described in FIG. 11.

Adaptor 300 is substantially cylindrically shaped with a cut out portion shown by arrow R. The cut out portion extends along the entire length of adaptor 300 in order to slide adaptor 300 over probe shaft 260 without disrupting ultrasound cable 236. Adaptor 300 also has rib 304 extending downwardly from the inner surface at the top portion of adaptor 300. Rib 304 extends along the length of adaptor 304 and engages groove 264 of probe shaft 260. Rib 304 prevents lateral movement of main body 226 with respect to shaft 260. Adaptor 300 further comprises backstop 306 extending upwardly from one end thereof. Backstop 306 keeps adaptor 300 axially positioned with respect to probe 256. Therefore, when set screw 290 is applied through hole 302 in adaptor 300, the entire unit remains securely fixed to probe 256 without risk of undesired axial or lateral movement.

To date there are no manufacturers of ultrasonic equipment that offer a single unit, permanent or disposable, that provides an effective sterile covering mechanism for use in operative procedures employing the transvaginal ultrasound probe. Prior art designed for this purpose rely on ineffective and time consuming multi-part systems that are either potentially hazardous during operation and/or fail to offer reasonable protection against patient contamination.

Figure 18:
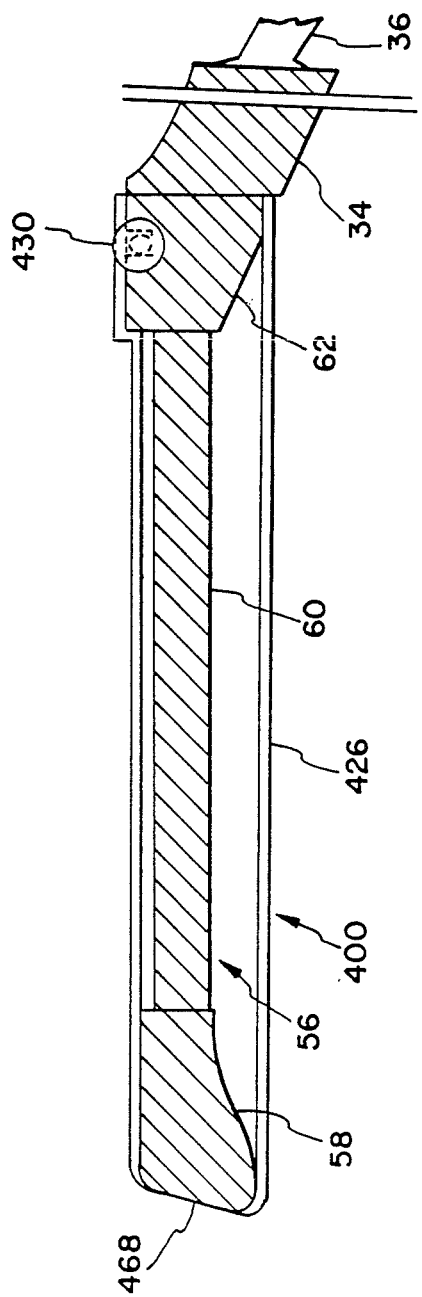
FIG. 18 is a schematic side view of another embodiment of the invention taken in section mounted over a transvaginal ultrasound probe.

FIG. 18 is a schematic side view of examination sheath 400 representing an extension of the present invention designed for daily non-operative vaginal ultrasound diagnostic examinations and is shown in place over the transvaginal probe described in FIG. 2. The main body of this extension is substantially similar to that described in FIG. 3, with the exception that it does not contain needle guide 28 or ultrasound cable sleeve 32. The shape of main body 426 is substantially the same as the apparatus in FIG. 3 and contains a similar window 468 and locking mechanism 430. This extension of the present invention is provided for daily diagnostic purposes in which a sterile operative field is not required.

Figure 19:
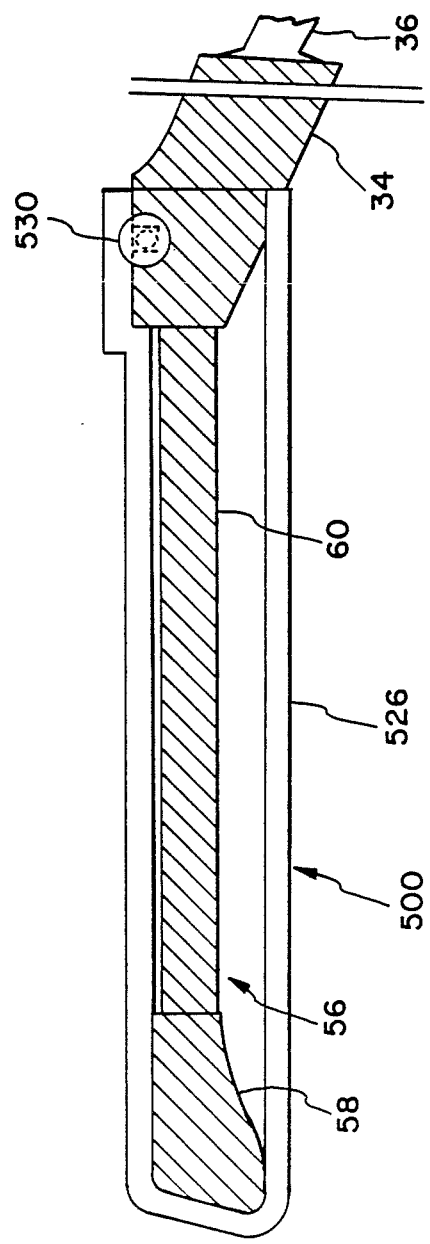
FIG. 19 is a schematic side view of another embodiment of the invention taken in section mounted over a transvaginal ultrasound probe.

FIG. 19 represents a schematic side view of a storage sheath 500 representing an additional extension of the present invention which is designed to serve as a storage sheath for the ultrasound probe when not in use. The storage sheath is substantially similar to the apparatus described in FIG. 3 but does not contain the thin walled ultrasound window 678 and walls 84 are constructed of thicker and more durable plastic in order to protect against accidental damage when the probe is not in use.

I claim:

1. A disposable combination needle guide and operative sheath adapted for use in surgical procedures on a transvaginal ultrasound probe comprising:
   a rigid hollow body having one closed and one open end, said open end sized to receive the insertion end of said probe;
   a sealed window in said body, said window being positioned at said closed end and permitting passage of ultrasonic waves therethrough without undue distortion;

an integral elongated needle or instrument passageway extending along a portion of said hollow body;

a flexible sleeve sealed to said open end and sized to receive said probe; and locking means associated with said hollow body to fix said hollow body in position with respect to said ultrasound probe.

2. Apparatus as defined in claim 1 wherein the closed end of said hollow body has an interior construction shaped to closely receive a head portion of said probe, said interior construction comprising a substantially flat roof, substantially flat side walls and a substantially circularly shaped floor.

3. Apparatus as defined in claim 1 wherein the closed end of said hollow body has an exterior construction comprising substantially circularly shaped top and bottom surfaces and substantially flat side walls.

4. Apparatus as defined in claim 1 wherein said window is formed from the same material as said hollow body and is integral therewith, said material having a thickness less than that of said hollow body.

5. Apparatus as defined in claim 1 wherein said passageway has a flared end to facilitate introduction of a needle or instrument into said passageway.

6. Apparatus as defined in claim 1 wherein the open end of said hollow body is substantially circularly shaped to closely receive a base portion of said probe.

7. Apparatus as defined in claim 1 wherein said hollow body further comprises an integral housing arm positioned near said open end to engage locking means.

8. Apparatus as defined in claim 1 wherein said lock means comprises a screw.

9. Apparatus as defined in claim 1 wherein said flexible sleeve is accordion shaped and longitudinally extendable.

10. Apparatus as defined in claim 1 wherein said flexible sleeve further comprises a pair of tabs mounted on an end opposite an end sealed to said hollow body to facilitate longitudinal flexing of said sleeve.

11. Apparatus as defined claim 1 wherein the closed end of said hollow body has a substantially circularly shaped interior construction and a smaller diameter than the open end of said hollow body to closely receive a head portion of said probe.

12. Apparatus as defined in claim 1 wherein the open end of said hollow body is substantially circularly shaped to closely receive a base portion of said probe.

13. Apparatus as defined in claim 1 wherein the closed end of said hollow body has a substantially circularly shaped interior construction to closely receive a head portion of said probe.

14. Apparatus as defined in claim 1 wherein the open end of said hollow body has a substantially circularly shaped interior construction and an interior diameter at least large as the interior diameter of said closed end.

15. Apparatus as defined in claim 1 further comprising an adapter partially surrounding a base portion of said probe and contained within the open end of said hollow body, said adapter comprising an elongated tube having a longitudinally extending opening to permit said adapter to slide over said probe, said adapter also having a v-shaped rib longitudinally extending along an interior roof surface to closely engage a v-shaped slot extending longitudinally along a top surface of said probe, said adapter having a hole in its side to permit passage of said locking means therethrough.

16. The combination of an ultrasonic probe and a disposable diagnostic sheath adapted for use in daily examination procedures on a transvaginal ultrasound probe, said sheath comprising:

a rigid hollow body having one closed end and one open end, said open end being sized to receive the insertion end of said probe;

a sealed window in said body, said window being positioned at said closed end and permitting passage of ultrasonic waves therethrough without undue distortion; and locking means associated with said hollow body to fix said hollow body in position with respect to said ultrasound probe.

17. The combination of an ultrasonic probe and a reusable protective sheath for storing said transvaginal ultrasound probe not in use, said sheath comprising:

a rigid hollow body having one closed end and one open end, said open end being sized to receive the insertion end of said probe; and locking means associated with said hollow body to fix said hollow body in position with respect to said ultrasound probe.

* * * * *